US006200304B1

(12) United States Patent
Schrader

(10) Patent No.: US 6,200,304 B1
(45) Date of Patent: Mar. 13, 2001

(54) TRANSFECTION SYSTEM, ITS PREPARATION AND USE IN SOMATIC GENE THERAPY

(75) Inventor: Jurgen Schrader, Düsseldorf (DE)

(73) Assignee: Cardiogene Gentherapeutische Systeme AG, Dusseldorf (DE)

( * ) Notice: Subject to any disclaimer, the term of this patent is extended or adjusted under 35 U.S.C. 154(b) by 0 days.

(21) Appl. No.: 09/112,519

(22) Filed: Jul. 9, 1998

(30) Foreign Application Priority Data

Jul. 11, 1997 (DE) .............................. 197 29 769

(51) Int. Cl.⁷ ..................... A61M 31/00; A61B 19/00

(52) U.S. Cl. ..................... 604/509; 604/500; 604/507; 128/898

(58) Field of Search ..................... 514/2, 12; 530/350, 530/412, 417, 422; 604/21, 102, 15, 16, 20, 41, 51–53, 104, 163, 171, 264; 607/116, 89; 435/320.1, 52–54, 85; 600/115, 373; 606/15, 16

(56) References Cited

U.S. PATENT DOCUMENTS

| | | |
|---|---|---|
| 5,112,305 | 5/1992 | Barath et al. . |
| 5,242,397 | 9/1993 | Barath et al. . |
| 5,328,470 | 7/1994 | Nabel et al. . |
| 5,702,304 * | 12/1997 | Umeyama et al. ............... 604/892.1 |
| 5,836,905 * | 11/1998 | Lemelson et al. ................ 604/21 |
| 5,873,852 * | 2/1999 | Vigil et al. ...................... 604/52 |

FOREIGN PATENT DOCUMENTS

| | | |
|---|---|---|
| 44 11 402 | 5/1995 | (DE) . |
| 44 11 402 | 10/1995 | (DE) . |
| 0001929 | 5/1979 | (EP) . |
| 0148605 | 7/1985 | (EP) . |
| 0753322 | 1/1997 | (EP) . |
| 0768098 | 4/1997 | (EP) . |
| WO 92 11895 | 7/1992 | (WO) . |
| WO 92/11895 | 7/1992 | (WO) . |
| WO 96/40325 | 12/1996 | (WO) . |
| WO 97/11738 | 4/1997 | (WO) . |
| WO 97/36633 | 10/1997 | (WO) . |
| WO 98 34667 | 8/1998 | (WO) . |
| WO 98/34667 | 8/1998 | (WO) . |

OTHER PUBLICATIONS

Chemical Reviews, vol. 90, No. 4, Jun., 1990 by Uhlmann et al.
The Second Annual International Symposium on Local Cardiovascular Drug Delivery, Oct. 13–15, 1996, Cambridge, MA.
M. Flugelman, Trombosis & Haemostasis, 1995, 74 (1), pp. 406–410.
Wilensky et al., Brief Reviews, TCM, vol. 3, No. 5, 1993.
IM. Flugelman, Vivo Gen Transfer, vol. 85, No. 3, 1992.
Ping Wu et al., Neurosci Lett (1995), 190(2), 73–6 Coden: Neled5;ISSN;0304–3940, 1995, XP002090359.
Yi Shi et al., Gene Ther. (1994), 1 (6), 408–14 Coden; Cirual; ISSN; 0969–7128, 1994 XP002090357.
Gregory Chapman, Circ–Res. (1992), 71 (1), 27–33 Coden; Cirual; ISSN; 0009–7330, 1992, XP002090360.
Reimer Riessen et al. Gene Ther. (1993), 4 (6), 749–758 Coden; HGTHE3; ISSN 1043–0342, 1993, XP002090358.
Wu, P. et al., Sendai virosomal infusion of an adeno–associated virus–derived construct containing neuropeptide Y into primary rat brain cultures, Neurosci. Lett. vol. 190(2), pp. 73–76 (1995).
Chapmann, G. et al., Gene Transfer into coronary arteries of intact animals with a percutaneous balloon catheter, Circ. Res. vol. 71(1), pp. 27–33 (1992).
Shi, Y. et al, Transgene expression in the coronary circulation: transcatheter gene delivery, Gene Ther. vol. 1(6), pp. 408–414 (1994).
Riessen, R. et al., Arterial gene transfer using pure DNA applied directly to a hydrogel–coated angioplasty balloon, Hum. Gene Ther., vol. 4(6), pp. 749–758 (1993).
Barath et al., "A Device for Combined Angioplasty and Intramural Site–Specific Treatment" Catheterization and Cardiovascular Diagnosis, 41:333–341 (1997).
Barath et al., "Nipple Balloon Catheter" Semin Intervent Cardiol., 1:43 (1996).
Barath et al., "Sterically stabilized ("stealth") lipsomes: potential carrier for high efficiency intramural delivery with infiltrator Angioplasty Balloon Center" Third Drug Delivery Meeting Abstract Book Thorax Center Rotterdam (Feb. 1997).
Website of IVT.
Product Information for INFILTRATOR® catheter by IVT.
Keith L. March, "Methods of local gene delivery to vascular tissues" Semin Intervant Cardio, 1:215–223 (1996).
Pavlides et al., "Intramural Drug Delivery by Direct Injection Within the Arterial Wall: First Clinical Experience With a Novel Intracoronary Delivery–Infiltrator System" Catheterization and Cardiovascular Diagnosis, 41:287–292 (1997).
Abstract of Angiology (2000), Apr. 51(4):289–94.
Abstract of Circulation (2000), Mar. 7; 101 (9):962–8.
Abstract of Catheter Cardiovascular Interv. (1999), Sep. 48(1):1–9.
Abstract of Am J Cardiol (1999), Jun. 1;83(11):1562–5, A7.
Abstract of Am J. Cardiol (1998), Feb. 15;81(4):401–6.
Abstract of Cathet Cardiovasc Diagn (1997), Jul.; 41(3):287–92.

(List continued on next page.)

*Primary Examiner*—Sharon Kennedy
*Assistant Examiner*—Michael J Hayes
(74) *Attorney, Agent, or Firm*—Frommer Lawrence & Haug LLP

(57) ABSTRACT

The present invention relates to a transfection system comprising one or more Infiltrator catheters, one or more non-viral nucleic acids, and, where appropriate, suitable ancillary substances and/or additives, and to its preparation and use in somatic gene therapy.

15 Claims, 5 Drawing Sheets

OTHER PUBLICATIONS

Figure 1:
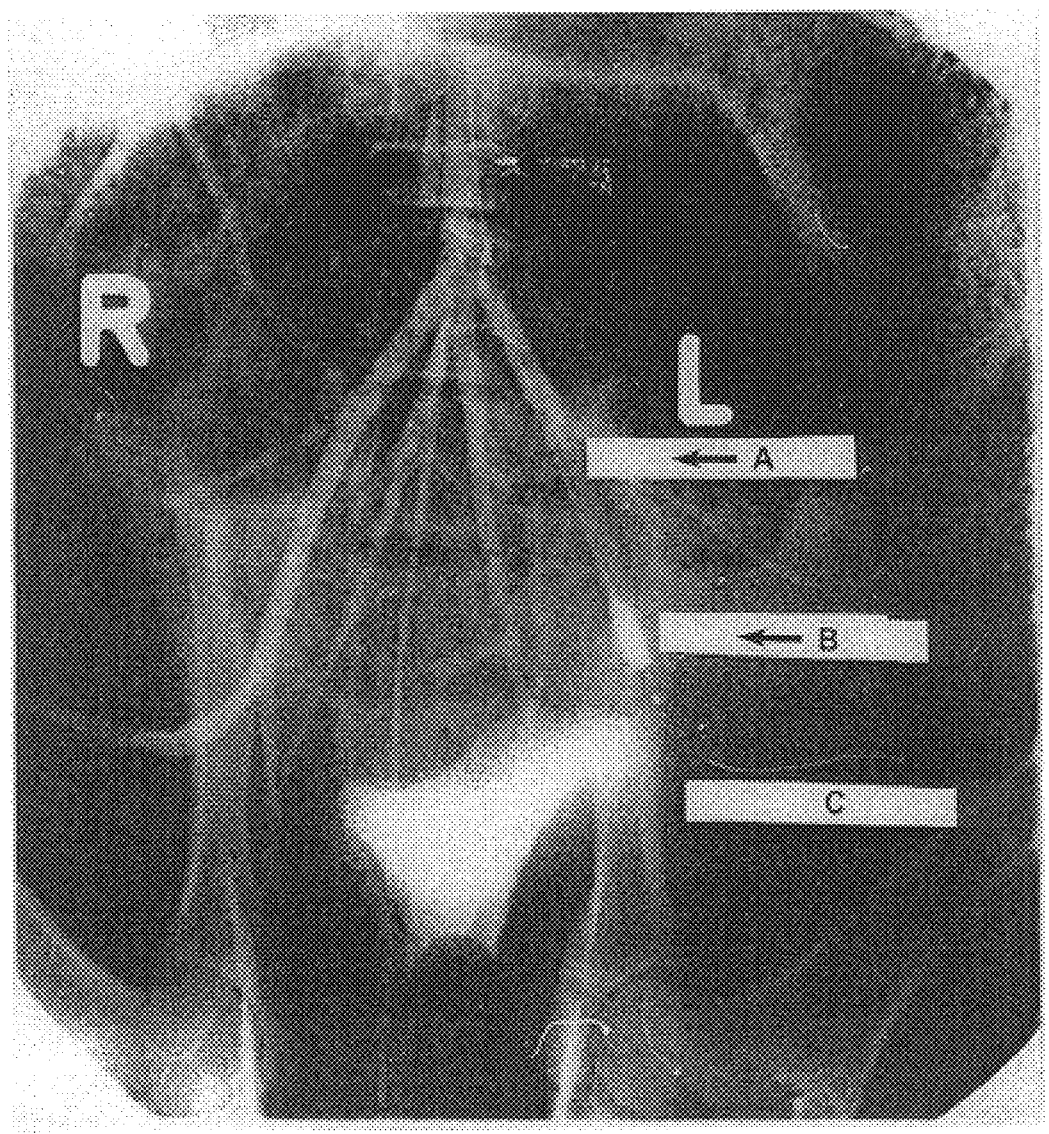

Orkin et al., Report and Recommendation of the Panel to Assess the NIH Investment in Research on Gene Therapy (Dec. 7, 1995).

Varenne et al., "Adenoviral Gene Transfer of Human Constitutive Endothelial Nitric Oxide Synthase to Injured Coronary Arteries" Journal of the American College of Cardiology, vol. 29(2), Supp. A, 380A (Feb. 1997).

Von der Leyen et al., Proc. Natl Acad Sci USA 92, 1137–1141 (1995).

Varenne et al., Circulation 98, 919–926 (1998).

Nabel et al., Science 249, 1285–1288 (1990).

Karas et al., J Am Coll Cardiol 20, 467–474 (1992).

Tahlil et al., "The Dispatch™ catheter as a delivery tool for arterial gene transfer" Cardiovascular Research, 33 pp 181–187 (1997).

Alfke et al., "Local Intravascular Drug Delivery: In Vitro Comparison of Three Catheter Systems" Cardiovascular Interventional Radiology, 212, 55–56 (1998).

* cited by examiner

TRANSFECTION SYSTEM, ITS PREPARATION AND USE IN SOMATIC GENE THERAPY

The present invention relates to a transfection system comprising one or more Infiltrator catheters, one or more nucleic acids, and, where appropriate, suitable ancillary substances and/or additives, and to its preparation and use in somatic gene therapy.

Local gene therapeutic treatment of vascular disorders represents a very promising prospect in interventional cardiology which might, for example, prevent reocclusion of vessels (restenosis) after mechanical widening of the blocked vessel with a balloon catheter (so-called percutaneous transluminal coronary angioplasty; PTCA), because restenosis still occurs in 30–40% of all cases after PTCA treatment.

Systemic administration of drugs has, despite very promising theoretical ideas, not produced an improvement in the long-term success of PTCA, presumably because the concentration of the therapeutic agent in the region of the treated stenosis was inadequate at the time. These results have led to the development of various special catheters permitting local treatment of a damaged section of vessel with specific drugs.

One disadvantage of the local administration of medicines, especially of medicines with a low molecular weight, using special catheters is, however, rapid perfusion out of the treated section of vessel. The required depot formation persists for only a short time.

A prolongation of the therapeutic effect can be achieved, for example, by therapeutically effective genes being transferred, by somatic gene transfer, locally into the vessel wall and being expressed there.

For gene transfer into the vessel wall, essentially three components are necessary:

A therapeutically effective gene which, on local expression, for example, results in the synthesis of a factor which inhibits restenosis formation.

A transfection system which permits
  (a) maximally efficient transfection of the vessel wall with the therapeutic gene and
  (b) localization of the transfection.

An efficient catheter technology which allows
  (a) in vivo transfections of specific individual sections of vessels in a hypo- or atraumatic manner using minimally invasive techniques,
  (b) in combination with the transfection system, minimal distribution of the therapeutic gene into the perivascular space or into the blood circulation to be ensured, and
  (c) a guarantee of short vessel occlusion times.

Schrader, J. & Gödecke, A. (DE 44 11 402) have now found that transfection with the nitric-oxide synthase gene in the form of a liposome complex in blood vessels leads to a therapeutically relevant inhibition of vessel stenosis and restenosis after PTCA. However, a polyethylene catheter was used for transfection with the DNA-liposome complexes, which interrupted the blood flow in the vessel for 15–20 minutes. In addition, transfection led to a thrombosis after reopening of the vessel in a few cases.

Some other special catheters have already been described in the literature with the intention of solving the problem of local administration of drugs (Wilenksy, R. L. et al. (1993) Trends Cardiovasc. Med. 3(5), 163–170).

For example, a double balloon catheter allows a defined section of vessel to be separated from the circulation by inflating balloons, one distal and one proximal of the section of vessel to be transfected (see, for example, Nathan, A. & Edelman E. R. (1995) in Edelman, E. R. (ed.), "Frontiers in Cardiology; Molecular Interventions and Local Drug Delivery" Saunders Company Ltd., london, GB, 29–52). The lumen isolated in this way is then filled with the therapeutic agent, which enters the vessel wall by diffusion. However, the disadvantages of this catheter are the long vessel occlusion times on use, and essentially only the innermost vessel cell layers are reached (Flugelman, M. Y. (1995), Thrombosis and Haemostasis, 74(1), 406–410). This type of catheter is therefore unsuitable for somatic gene transfer.

The porous balloon was developed in order to force a therapeutic agent under pressure through pores in an inflated balloon into the vessel wall and thus to achieve transmural distribution of the therapeutic agent. The high pressures required for the injection (2–5 atm.) frequently resulted, however, in serious mechanical damage to the vessel wall, which was manifested either by dissection or the development of necrotic zones in the media. In addition, the transfection efficiency is extremely low and not localized (Flugelman, M. Y. (1995), supra; Flugelman, M. Y. et al. (1992) Circulation, 85(3), 1110–1117). This type of catheter was therefore also found to be unsuitable for somatic gene transfer.

The principle of the functioning of the Dispatch catheter resembles in principle the double balloon catheter described above (see, for example, McKay, R. G. et al. (1994), Catheterization and Cardiovascular Diagnosis, 33, 181–188). The section of vessel to be treated is, however, in this case not separated from the remainder of the circulation by two peripheral balloons but is separated by a coil which makes contact with the vessel wall after inflation. The vectors are injected into the closed chamber through orifices in the catheter shaft between the helical elements. Transfection takes place by diffusion. In order to make the required long transfection time of about 30 minutes possible without cutting off the distal regions from the blood flow, a conduit passing through the shaft of the inflated catheter was fitted to make blood flow possible.

The needle injection catheter (NIC) is characterized by three injection needles which can be advanced out of the rounded tip of a catheter and then penetrate into the vessel wall (see, for example, Gonschior, P. et al. (1995) Coronary Artery Disease, 6, 329–344). It has already been possible to inject drugs through these needles into the vessel wall.

However, manipulation of the NIC is difficult because it is not easily possible to check how far the needles have emerged from the head of the catheter, although this defines the depth of injection. This entails the risk of perforation of the vessel wall and thus transfection of perivascular tissue, but also of bleeding from the vessel. This danger applies particularly on transfection of eccentric plaques.

Janssens, S. et al., The Second Annual International Symposium, Oct. 13–15, 1996, Cambridge, Mass., describe gene transfer with the aid of an adenoviral vector and of an Infiltrator catheter which is not described in detail. However, the disadvantage of this transfection system is that cytotoxic effects have been observed with adenoviral vectors (Flugelman, M. Y. (1995), supra).

It was therefore an object of the present invention to find a transfection system which makes it possible to perform somatic gene transfer into vessels efficiently and with minimum damage.

The present invention therefore relates firstly to a transfection system comprising one or more Infiltrator catheters, one or more nucleic acids in nonviral form and, where appropriate, suitable ancillary substances and/or additives.

The Infiltrator catheter is a special catheter developed for intravascular injection of drugs into the vessel wall. It takes the form of a balloon catheter from whose surface injector ports (tubular, stud-like extensions for administering one or more active substances) project. The height of the injector ports is normally about 100–500 µm, preferably about 100–250 µm, in particular about 100 µm, and the number of injector ports per balloon is normally about 5×7, preferably about 3×7. Inflation of the balloon to, normally, about 2 atm forces these injector ports into the vessel wall. It is then possible to inject through the injector ports in general up to about 500 µl, preferably about 250–300 µl, of active substance or active substances under low pressure, preferably about 100–200 mm Hg, in particular about 150 mm Hg, into the vessel wall.

The catheter normally has more than one lumen and is, in particular, a double lumen, particularly preferably a triple lumen, catheter.

The double lumen catheter generally consists of a tubular shaft and the inflatable balloon which has been mentioned and which envelops a suitable point on the shaft. The shaft comprises at the point where the balloon is one or more orifices to which the balloon can be inflated and the active substance can enter the balloon. The active substance passes from there through the injector port into the vessel wall. A double lumen Infiltrator catheter as described in U.S. Pat. No. 5,112,305 or U.S. Pat. No. 5,242,397 is particularly preferred.

A triple lumen Infiltrator catheter which comprises a central tubular shaft, an inflatable balloon which envelops the shaft at a suitable point, and a tubular sleeve which comprises the said injector ports at the point where the inflatable balloon is, is particularly preferred. After positioning of the catheter, the balloon is inflated, whereupon the said sleeve with the injector ports is pressed against the vessel wall. The active substance is then introduced into the tubular sleeve in order to pass from there through the injector ports into the vessel wall. A particularly preferred triple lumen Infiltrator catheter is a catheter as described in EP 0 753 322 A1 or EP 0 768 098 A2.

The transfection system according to the invention generally additionally comprises a guide wire which makes correct positioning of the catheter possible.

The nucleic acid of the transfection system according to the invention is present in nonviral form, preferably as single- or double-stranded DNA or as RNA, for example as naked nucleic acid or together with other nonviral components.

The term "nonviral" means according to the present invention that the nucleic acid is not transfected with the aid of genetically manipulated viral vectors such as, for example, retroviral, adenoviral or adeno-associated viral vectors. The use of, for example, Sendai viruses in the form of virosomes (see below) is not precluded by the term "nonviral".

A suitable naked nucleic acid is, for example, a nucleic acid in the form of a plasmid DNA or of a so-called antisense oligonucleotide (see, for example, Uhlmann, E. & Peyman, A. (1990) Chemical Reviews, 90, 543–584, No. 4).

Nucleic acids effective for gene therapy can also be obtained by complexation of the required nucleic acid with other nonviral components, preferably liposomes, since this makes it possible to achieve a very high transfection efficiency, in particular of the vessel wall (see, for example, DE 44 11 402 A1). Transfection with nucleic acid/liposome complexes using Sendai viruses in the form of so-called HVJ liposomes (virosomes) is particularly advantageous because this makes it possible to increase the transfection rate still further.

In lipofection, small unilamellar vesicles of, for example, cationic lipids are prepared by ultrasound treatment of the liposome suspension. The nucleic acid is ionically bound to the surface of the liposomes, in particular in a ratio such that a net positive charge remains and the nucleic acid is 100% complexed by the liposomes. Besides the lipid mixtures employed by Felgner et al. (Felgner, P. L. et al. (1987), Proc. Natl. Acad. Sci. USA, 84, 7413–7414), DOTMA (1,2-dioleyloxy-3-propyltrimethylammonium bromide) and DOPE (dioleylphosphatidylethanolamine), numerous new lipid formulations have now been synthesized and tested for their efficiency in transfecting various cell lines (Behr, J.P. et al. (1989), Proc. Natl. Acad. Sci. USA, 86, 6982–6986; Felgner, J. H. et al. (1994) J. Biol. Chem., 269, 2550–2561; Gao, X. & Huang, L. (1991), Biochim. Biophys. Acta, 1189, 195–203). Examples of the new lipid formulations are DOTAP N-[1-(2,3-dioleoyloxy)propyl]-N,N,N-trimethylammonium methyl sulphate or DOGS (TRANSFECTAM; dioctadecylamidoglycylspermine). One example of the preparation of DNA/liposome complexes from phosphatidylcholine, phosphatidylserine and cholesterol and successful use thereof in the transfection of vessel walls using Sendai viruses is described in DE 44 11 402.

It is particularly advantageous for the nucleic acid/liposome complex to comprise nucleic acid binding proteins, for example chromosomal proteins, preferably HMG proteins (high mobility group proteins), in particular HMG-1 or HMG-2, or nucleosomal histones such as H2A, H2B, H3 or H4, because this makes it possible to increase the expression of the required nucleic acid by at least 3–10-fold. The chromosomal proteins can, for example, be isolated from calf thymus or rat liver by generally known methods or be prepared by genetic manipulation. Human HMG-1 can, for example, be prepared particularly straightforwardly by genetic manipulation by methods known to the skilled person using the human cDNA sequence from Wen, L. et al. (1989) Nucleic Acids Res., 17(3), 1197–1214.

The required nucleic acid is generally a nucleic acid which codes for a therapeutically effective gene product.

Examples of nucleic acids which code for a therapeutically effective gene product are the nitric-oxide synthase gene, especially a gene which codes for inducible nitric-oxide synthase (see, for example, DE 44 11 402 A1), the erythropoietin gene (see, for example, EP 0 148 605 B1), the insulin gene (see, for example, EP 0 001 929 B1) or the genes coding for blood coagulation factors, interferons, cytokines, hormones, growth factors etc. Particularly preferred genes are those coding for proteins which occur in blood. The somatic gene therapy according to the invention of the vessel wall can eliminate or alleviate in a particularly simple and lasting manner for example a pathological deficiency phenomenon such as, for example, a deficiency of insulin in diabetics, a deficiency of factor VIII in haemophiliacs, a deficiency of erythropoietin in kidney patients, a deficiency of thrombopoietin or a deficiency of somatostatin associated with stunted growth, by increasing the plasma concentrations of the particular active substance. The present invention is therefore not limited just to the therapy of purely vascular disorders such as, for example, arteriosclerosis, stenosis or restenosis, but is generally applicable.

It is also advantageous for the described use for gene therapy if the part of the nucleic acid which codes for the polypeptide comprises one or more non-coding sequences including intron sequences, preferably between promoter and the polypeptide start codon, and/or a polyA sequence, in particular the naturally occurring polyA sequence or an SV40 virus polyA sequence, especially at the 3' end of the gene, because this can achieve stabilization of the mRNA in the cell (Jackson, R. J. (1993) Cell, 74, 9–14 and Palmiter, R. D. et al. (1991) Proc. Natl. Acad. Sci. USA, 88, 478–482).

The transfection system according to the invention can be produced in a simple manner by combining one or more of the Infiltrator catheters which are described above or can be purchased, one or more of the nucleic acids described above, where appropriate suitable ancillary substances and/or additives and, where appropriate, a guide wire.

Examples of suitable ancillary substances and/or additives are those known to a skilled person in the form of stabilizers, such as nuclease inhibitors, preferably complexing agents such as EDTA, protease inhibitors or alkaline earth metal solutions, especially on use of Sendai viruses in the transfection system according to the invention, such as, for example, a $CaCl_2$ solution, which is preferably added before transfection with virosomes.

The described Infiltrator catheter is suitable and advantageous in the form of the transfection system according to the invention for somatic gene therapy, especially for treating vascular disorders, genetic disorders and/or disorders which can be treated by gene transfer, including prevention thereof, as already described in detail above by way of example.

The present invention therefore also extends to the use of an Infiltrator catheter for producing a transfection system according to the invention, preferably for somatic gene therapy. The present invention further extends to the use of the transfection system according to the invention for somatic gene transfer, in particular for the treatment or prevention of the disorders described.

The unexpected advantage of the present invention derives from the fact that, in contrast to other transfection systems described in the literature, which have been developed for local administration of pharmaceuticals, an Infiltrator catheter is particularly suitable according to the present invention for the transfer of one or more nucleic acids in somatic gene therapy. It was possible to position the Infiltrator catheter accurately in the vessel and, on inflation of the balloon, it led to leak-free occlusion of the vessel so that the injector ports were pressed by the balloon into the vessel wall, and the injection of the nucleic acid(s) could take place effectively under low pressure, which resulted in only minimal changes in the vessel wall. This made it possible to achieve, with short vessel occlusion times (maximally about 30 seconds), efficient transfection of the vessel wall and high and permanent expression of the required nucleic acid.

The following figures and examples are intended to illustrate the invention in detail without restricting it thereto.

DESCRIPTION OF THE FIGS.

FIG. 1 shows a radiograph of the iliac vascular system of a pig during transfection of the left iliac artery. The film shows an inflated Infiltrator catheter (B) in the iliac artery (A) of the pig. The guide wire used to introduce the catheter (C) is evident distal of the catheter. The leak-proof occlusion of the vessel by the inflated balloon is evident from the lack of contrast in the distal femoral arteries (compare right-hand side).

Figure 2A:
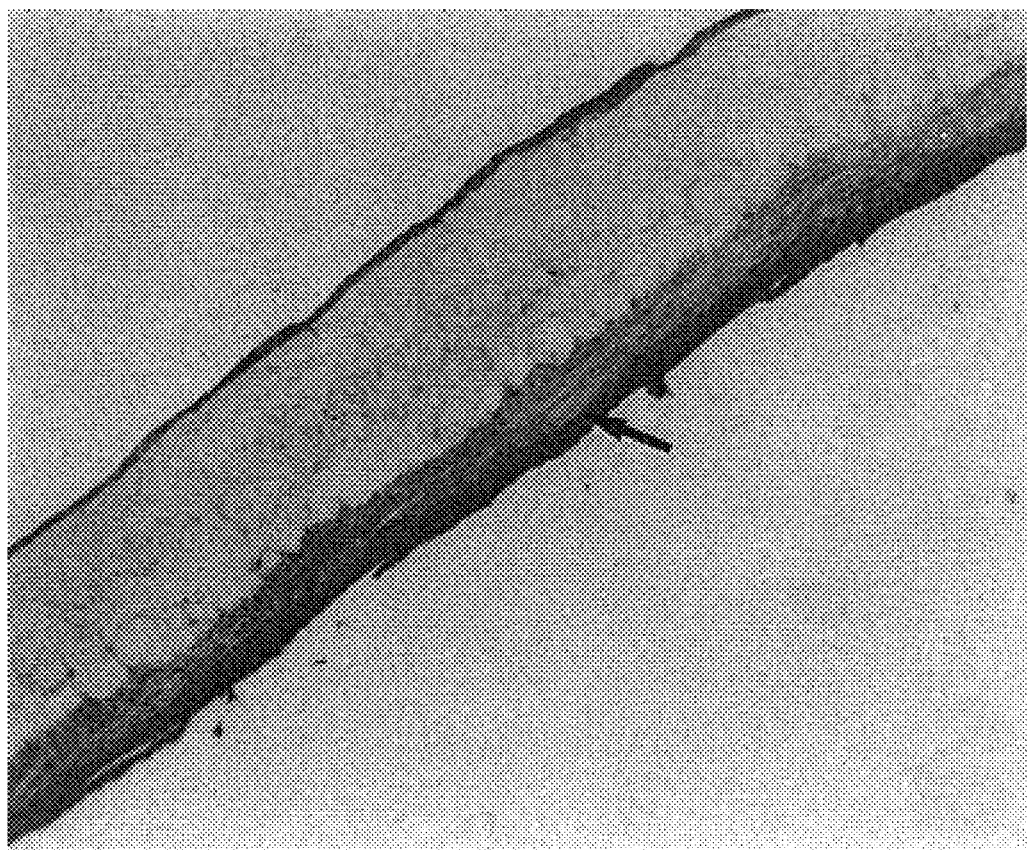
Figure 2B:
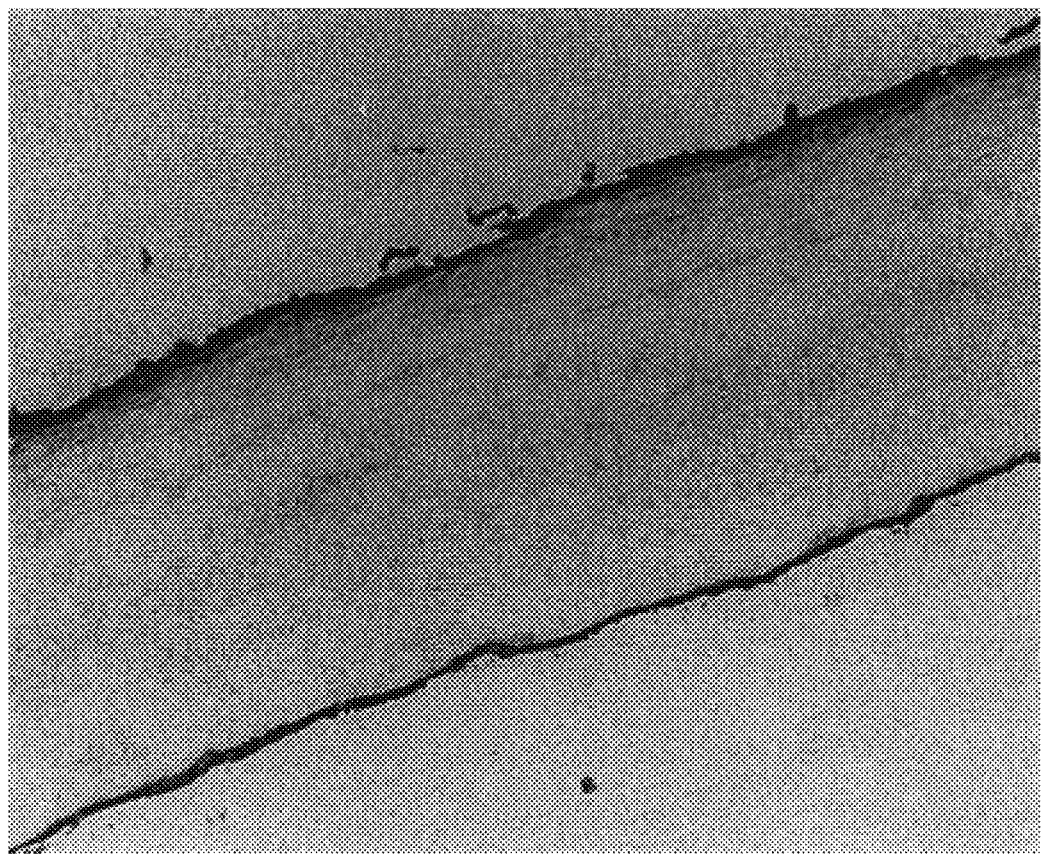

FIGS. 2a and b show the immunohistochemical detection of iNOS expression in iliac arteries of the pig after transfection with the control vector (FIG. 2a) and with the pSCMV-iNOS vector (FIG. 2b). The dark colour in FIG. 2b (arrow) indicates strong iNOS expression.

Figure 3A:
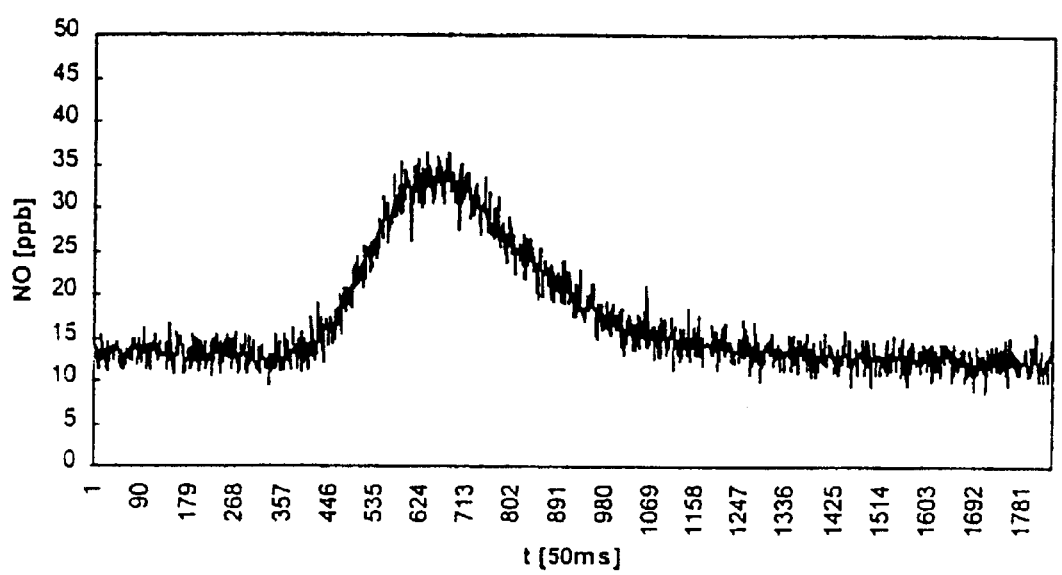
Figure 3B:
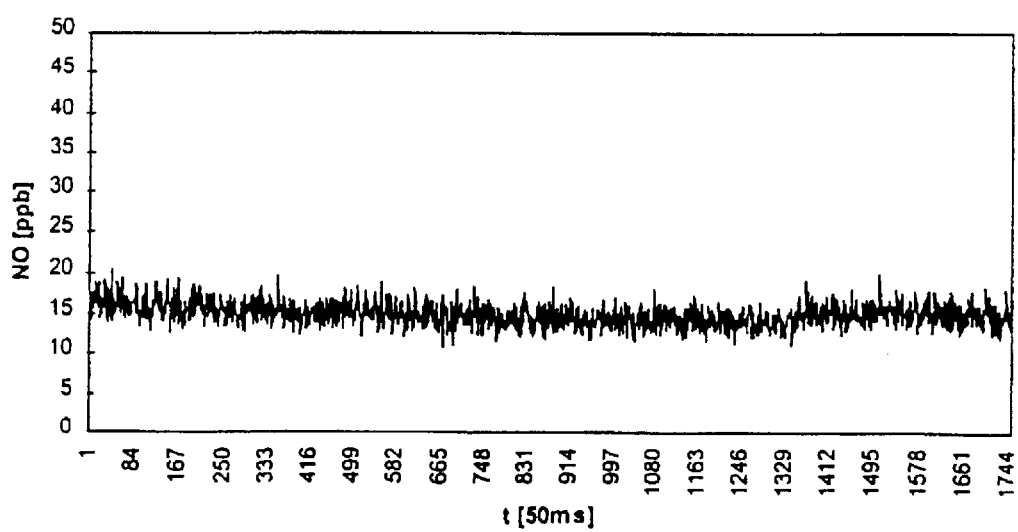

FIGS. 3A and B show detection of NOx accumulation in culture supernatant from vessels transfected either with the pSCMV-iNOS vector (A) or with the control vector (B). Whereas no NOx signal is detectable in the control segment (FIG. 3B), there is clear NOx release in the transfected vessel (FIG. 3A). (ppB=parts per billion)

EXAMPLE

Expression of the Inducible Nitric-Oxide Synthase Gene in the Pig Femoral Artery 1. Transfection protocol
1.1 Preparation of the DNA 200 μg of the gene transfer vector pSCMV-iNOS which codes for the inducible mouse nitric-oxide synthase (DE 44 11 402 A1), in a concentration of 2 μg/μl dissolved in TE buffer (10 mM Tris.HCl, pH 7.4), were mixed with 64 μg of HMG-1 protein from calf thymus, dissolved in BSS buffer (140 mM NaCl, 5.4 mM KCl, 10 mM Tris.Cl, pH 7.6), and the solution was adjusted to a final volume of 200 μl with BSS buffer. The resulting solution was incubated at 37° C. for 30 min.

1.2 Liposome preparation 5 mg portions of a lipid mixture consisting of phosphatidylcholine (PC), cholesterol (C) and phosphatidylserine (PS) with a ratio by weight in a mixture of 4.8:2:1 were dissolved in 2 ml of diethyl ether. 200 μl of the DNA solution prepared in Example 1.1 were added to the dissolved lipids. The mixture was then homogenized by vortexing for 2 min and subsequently sonicated in an ultrasonic bath for 10 sec. The ether was then evaporated in a rotary evaporator at 37° C. The remaining emulsion was subsequently vortexed for about 2 min until an opalescence appeared.

1.3 Preparation of the Sendai viruses

Sendai viruses were grown by standard methods in chorioallantoic fluid from fertilized chicken eggs (Nakanishi, M. et al. (1985) Exp. Cell. Res., 159(2), 399–409). The viruses were subsequently purified by the following centrifugation method in a Sorvall GSA rotor at 4° C.:

| | |
|---|---|
| 1. Chorioallantoic fluid: | 10 min at 3000 rpm |
| 2. Supernatant: | 30 min at 13,000 rpm |
| 3. Pellet: | suspended in BSS buffer |
| 4. Suspension: | 10 min at 3000 rpm |
| 5. Supernatant: | 30 min at 13,000 rpm |
| 6. Pellet: | resuspended in BSS buffer. |

The titre was then adjusted to 16,000 haemagglutination units (HAU)/ml. Shortly before use, the viruses were inactivated by UV irradiation with 11 $J/m^2 \cdot s$.

1.4 Preparation and purification of the virosomes (HVJ liposomes)

1 ml of the UV-inactivated viruses prepared as in Example 1.3 (16,000 HAU) were mixed with the liposomes prepared as in Example 1.2 and incubated on ice for 10 min. The suspension was then shaken for fusion of the viruses with the liposomes on an orbital shaker (120 rpm, 37° C.) for 60 min. The virosomes which were formed were then removed from the unincorporated viruses by ultracentrifugation through a sucrose cushion (30% sucrose) in a TH641 rotor, Sorvall Instruments, at 28,000 rpm and at 4° C. The virosomes in this case banded on the sucrose cushion, and the unincorporated viruses sedimented to the bottom of the tube. The virosomes were then removed and stored on ice until transfected. Shortly before carrying out the transfection, $CaCl_2$ was added to a final concentration of 2 mM.

1.5 Transfection

Transfection took place by injecting 300 μl of the virosomes prepared as in Example 1.4 (8–10 μg of pSCMV-iNOS entrapped in HVJ liposomes, about 1000 HAU) through the described catheter into the iliac artery of Munich minipigs. The injection took about 10 sec. Virosomes which contained the vector pSCMV2 (DE 44 11 402 A1) were employed as control.

2. Surgical procedures

The left carotid artery was exposed by a surgical procedure and a 7-F or 9-F support was inserted by a modified Seldinger technique. All further angiographic or procedural steps took place via this support. Firstly, a survey angiography of the distal aorta and of the iliac vessels was performed via a calibration pigtail catheter. The catheter for local transfection was then advanced over a guide wire as far as the femoral arteries. The transfection solution was then introduced through a lateral injector port in accordance with the manufacturer's instructions for the local administration of drugs into the vessel. In this case, expression vector and control vector were respectively injected into the right and left femoral arteries of the same animal. After removal of the catheter, the carotid artery was closed by suturing the vessel. The wound was then closed.

3. Immunohistochemical detection

Frozen sections (8 μm) of the transfected vessel wall sections were reacted with monoclonal anti-iNOS antibodies (Transduction Laboratories, #N32020). Antibody binding was detected via a streptavidin/peroxidase complex using biotinylated anti-mouse antibodies (Vector Laboratories, #BA-2000) with the Vecta Stain Elite kit (Vector Laboratories, #PK-6100;).

4. Biochemical detection

In addition to the immunohistochemistry, increased NO formation by the transfected vessels was directly detected on the basis of the accumulation of nitrate/nitrite (NOx) in the culture supernatant from explanted transfected vessel sections. Transfected vessel sections were incubated in Krebs-Hensel light buffer (in mmol/L: 116 NaCl; 4.6 KCl; 1.1 $MgSO_4$; 24.9 $NaHCO_3$; 2.5 $CaCl_2$; 1.2 $KH_2PO_4$; 10 glucose and 0.5 EDTA equilibrated with 95% $O_2$ and 5% $CO_2$ (pH 7.4; 37° C.)). Incubation took place at 37° C. for 24 h. The NOx accumulation was determined after reducing in nitrate+nitrite to NO by a chemiluminescence method (nitric oxide analyzer NOA 280; Sievers Inc., USA).

5. Results 5.1 The Dispatch catheter

Use of a Dispatch catheter did not result in efficient transfection because it was not possible to produce a tightly closed isolated chamber by inflation of the helical elements. Injection of the vectors through the catheter shaft does not lead to a rise in pressure, which would be expected with a closed chamber. The leakiness of the chamber was demonstrated by the rapid flowing out of X-ray contrast medium from the chamber. The Dispatch catheter is therefore unsuitable for local gene transfer.

5.2 The Infiltrator catheter

In contrast to the Dispatch catheter or needle injection catheter, accurate positioning (see FIG. 1) was possible with the Infiltrator catheter (Barath drug delivery catheter with 3×7 injector ports in the longitudinal axis with the cylindrical shape of the ports, which have a slight upward conical taper, model No. DD140015, Interventional Technologies Europe Ltd., Ireland), and inflation of the balloon resulted in tight closure of the vessel.

As shown in FIG. 2, a pronounced immune reactivity was detectable in the transfected vessel sections and extended up to 50% of the vessel wall diameter. The control-transfected vessels lacked the corresponding stain, so that this detection specifically showed expression of iNOS.

FIG. 3 shows that a distinctly increased NOx release was obtained after transfection by comparison with sections transfected with the control vector.

It was thus possible with the Infiltrator catheter to show efficient in vivo transfection of the vessel wall, which extended up to 50% of the vessel wall diameter, with short vessel occlusion times (max. 30 s).

What is claimed is:

1. A method of delivering a composition comprising one or more non-viral nucleic acids to a vessel wall which comprises administering said nucleic acids by a catheter which comprises a central tubular shaft, an inflatable balloon, which envelopes the shaft at the distal end, and a tubular sleeve that envelops the balloon which comprises one or more injector parts.

2. The method according to claim 1, wherein the injection ports have a height of about 100 to 500 μm.

3. The method according to claim 1, which comprises 3×7 injector ports.

4. The method according to claim 1, wherein the catheter comprises more than one lumen.

5. The method according to claim 1, wherein the catheter further comprises a guidewire.

6. The method according to claim 1, wherein the non-viral nucleic acid is selected from the group consisting of a nucleic acid in naked form and a nucleic acid together with other non-viral components.

7. The method according to claim 1, wherein the non-viral nucleic acid is selected from the group consisting of a single-stranded DNA, a double-stranded DNA and an antisense oligonucleotide.

8. The method according to claim 1, wherein the non-viral nucleic acid is present in the form of a nucleic acid/liposome complex.

9. The method according to claim 8, wherein the nucleic acid/liposome complex further comprises one or more nucleic acid binding proteins.

10. The method according to claim 1, wherein the nucleic acid codes for a therapeutically effective gene product.

11. The method according to claim 10, wherein the gene product is a nitric-oxide synthetase.

12. The method according to claim 11, wherein the nitric-oxide synthetase is iNOS.

13. The method according to claim 11, wherein the nucleic acid coding for therapeutically effective gene product comprises one or more noncoding sequences and/or a poly A sequence.

14. The method according to claim 11, wherein the composition further comprises ancillary substances or additives.

15. A method for treating and preventing vascular disorders, genetically related disorders and/or disorders which can be treated by gene transfer in a host in need thereof, which comprises delivering one or more nonviral nucleic acids to a vessel wall in said host by a catheter which comprises a central tubular shaft, an inflatable balloon, which envelopes the shaft at the distal end, and a tubular sleeve that envelopes the balloon, which comprises one or more injector ports.

* * * * *